(12) United States Patent
Govari et al.

(10) Patent No.: US 10,722,139 B2
(45) Date of Patent: Jul. 28, 2020

(54) NAVIGATION OF AN ANGIOPLASTY GUIDEWIRE

(71) Applicant: BIOSENSE WEBSTER (ISRAEL) LTD., Yokneam (IL)

(72) Inventors: Assaf Govari, Haifa (IL); Yaron Ephrath, Karkur (IL); Vadim Gliner, Haifa (IL); Shai Shimon Bard, Zichron Yaakov (IL); Andres Claudio Altmann, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 1046 days.

(21) Appl. No.: 14/623,335

(22) Filed: Feb. 16, 2015

(65) Prior Publication Data
US 2016/0235336 A1    Aug. 18, 2016

(51) Int. Cl.
*A61B 5/06* (2006.01)
*A61M 25/09* (2006.01)
(Continued)

(52) U.S. Cl.
CPC .............. *A61B 5/062* (2013.01); *A61B 5/063* (2013.01); *A61B 5/6851* (2013.01);
(Continued)

(58) Field of Classification Search
CPC ..... A61B 5/062; A61B 5/6876; A61B 5/6851; A61B 5/063; A61M 25/09; A61M 2025/09141
See application file for complete search history.

(56) References Cited

U.S. PATENT DOCUMENTS

| | | |
|---|---|---|
| 5,372,144 A | 12/1994 | Mortier et al. |
| 7,317,819 B2 | 1/2008 | Janes |

(Continued)

FOREIGN PATENT DOCUMENTS

| | | |
|---|---|---|
| CN | 102118994 A | 7/2011 |
| CN | 102525657 A | 7/2012 |

(Continued)

OTHER PUBLICATIONS

St. Jude Medical CPS Excel™ MediGuide Enabled™ Guidewire and accessories FDA approval document, Section 5-510(k) Summary, May 2012 and FDA letter dated Jun. 2012.
(Continued)

*Primary Examiner* — Angela M Hoffa (57) ABSTRACT

A method, including advancing a guidewire having a first diameter through a patient lumen, the guidewire being tracked by an electromagnetic system and an impedance system. While advancing the guidewire, signals of both systems, that are generated in response to differing positions of the guidewire in the lumen, are recorded. The method includes recording correspondences between the signals at each of the differing positions. The method also includes withdrawing the guidewire from the lumen, and then advancing through the lumen a second guidewire, having a second diameter smaller than the first diameter, which is tracked by the impedance system. While advancing the second guidewire, a signal of the impedance system generated in response to advancement of the second guidewire in the lumen is received. The method includes applying the correspondences to the signal in order to determine a position of the second guidewire in the lumen.

8 Claims, 5 Drawing Sheets

(51) Int. Cl.
*A61B 34/20* (2016.01)
*A61B 5/00* (2006.01)
(52) U.S. Cl.
CPC ............ *A61B 5/6876* (2013.01); *A61M 25/09* (2013.01); *A61B 2034/2051* (2016.02); *A61M 2025/09141* (2013.01)

(56) References Cited

U.S. PATENT DOCUMENTS

| | | | |
|---|---|---|---|
| 7,536,218 B2* | 5/2009 | Govari | A61B 5/0538 600/424 |
| 7,848,789 B2* | 12/2010 | Govari | A61B 5/0538 600/424 |
| 8,043,351 B2 | 10/2011 | Yon et al. | |
| 8,373,017 B2 | 2/2013 | Wu et al. | |
| 8,456,182 B2 | 6/2013 | Bar-Tal | |
| 8,473,030 B2 | 6/2013 | Greenan et al. | |
| 8,478,383 B2* | 7/2013 | Bar-Tal | A61B 5/063 600/424 |
| 8,632,468 B2 | 1/2014 | Glossop et al. | |
| 8,636,718 B2 | 1/2014 | Sela et al. | |
| 8,764,683 B2 | 7/2014 | Meller et al. | |
| 10,029,071 B2* | 7/2018 | Hannon | A61M 25/0017 |
| 2006/0074442 A1 | 4/2006 | Noriega et al. | |
| 2006/0173298 A1 | 8/2006 | Tucker | |
| 2007/0021731 A1 | 1/2007 | Garibaldi et al. | |
| 2009/0247878 A1 | 10/2009 | Tanioka et al. | |
| 2011/0130750 A1 | 6/2011 | Ornsby et al. | |
| 2011/0230758 A1 | 9/2011 | Eichler | |
| 2012/0172761 A1* | 7/2012 | Meller | A61B 5/062 600/585 |
| 2013/0072943 A1 | 3/2013 | Parmar | |
| 2014/0046216 A1 | 2/2014 | Palme, Jr. et al. | |
| 2014/0081204 A1 | 3/2014 | Cohen et al. | |
| 2014/0358123 A1* | 12/2014 | Ueda | A61M 25/0097 604/510 |
| 2015/0297863 A1* | 10/2015 | Hannon | A61M 25/0009 604/544 |
| 2016/0235336 A1* | 8/2016 | Govari | A61B 5/062 |

FOREIGN PATENT DOCUMENTS

| | | | |
|---|---|---|---|
| EP | 2 085 108 A3 | 12/2009 | |
| EP | 2465430 A1 * | 6/2012 | ............ A61B 5/063 |
| JP | 2012125579 A | 7/2012 | |
| WO | 2009129475 A1 | 10/2009 | |
| WO | 2010022370 A1 | 2/2010 | |
| WO | 2012066552 A1 | 5/2012 | |

OTHER PUBLICATIONS

European search report from corresponding European patent application No. 16155636.0, dated Jul. 7, 2016.
Australian Examination report for related application No. 2016200819, dated Aug. 28, 2019.
Australian Examination report for related application No. 2016200681, dated Aug. 29, 2019.
Chinese office action for corresponding Chinese patent application No. 2016-025652, dated Dec. 24, 2019.
Japanese office action for corresponding Japanese patent application No. 201610087299.8, dated Nov. 19, 2019.

* cited by examiner

NAVIGATION OF AN ANGIOPLASTY GUIDEWIRE

CROSS-REFERENCE TO RELATED APPLICATION

This application is related to U.S. patent application titled Angioplasty Guidewire, filed on even date with the present application, and which is incorporated herein by reference.

FIELD OF THE INVENTION

The present invention relates generally to invasive medical procedures, and specifically to navigation of a guidewire used in such procedures.

BACKGROUND OF THE INVENTION

In inserting a guidewire into a patient during a medical procedure such as angioplasty, it is important that the guidewire follows a correct path. One method for tracking a guidewire is to use X-rays. However, X-rays are ionizing radiation and it is preferable to reduce a patient's exposure to X-rays as much as possible.

U. S. Patent Application 2011/0230758 to Eichler, whose disclosure is incorporated herein by reference, describes a system for determining the position of the tip of a medical catheter within the body of a patient. The method includes inserting a mapping position system catheter into a tubular organ, and inserting a medical catheter into the organ.

U.S. Pat. No. 8,632,468 to Glossop et al., whose disclosure is incorporated herein by reference, describes a system for assisting/performing image-guided transjugular intrahepatic portosystemic shunt (TIPS) procedures in a portion of an anatomy of a patient. The system includes a guide needle portion having a hollow tube with a bend toward its distal tip, and a puncture needle portion that includes at least one position indicating element at its tip.

U.S. Pat. No. 8,043,351 to Yon et al., whose disclosure is incorporated herein by reference, describes a method for performing a therapy for angioplasty. The disclosure refers to a balloon tipped catheter, and describes how mapping electrodes may be employed at the distal end of a warm balloon.

U.S. Pat. No. 7,317,819 to Janes, whose disclosure is incorporated herein by reference, describes apparatus for three-dimensional imaging. The disclosure refers to viewing a specific portion of a three-dimensional image exposure, e.g., for viewing an angioplasty device moving through a vein or artery.

U.S. Patent Application 2006/0173298 to Tucker, whose disclosure is incorporated herein by reference, describes methods for using a catheter to generate a geographic map of a venous structure of the heart and to generate an electrical map of the electrical conduction patterns of the heart for locating an aberrant electrical conduction pattern.

U.S. Patent Application 2014/0081204 to Cohen et al., whose disclosure is incorporated herein by reference, describes a remotely controlled catheter insertion system which may include a mapping procedure and an angioplasty procedure.

Documents incorporated by reference in the present patent application are to be considered an integral part of the application except that, to the extent that any terms are defined in these incorporated documents in a manner that conflicts with definitions made explicitly or implicitly in the present specification, only the definitions in the present specification should be considered.

SUMMARY OF THE INVENTION

An embodiment of the present invention provides a method, including:

advancing a first guidewire having a first diameter through a lumen in the body of a patient, the first guidewire being configured to be tracked by an electromagnetic tracking system and an impedance tracking system;

while advancing the first guidewire, recording first signals of the electromagnetic tracking system and second signals of the impedance tracking system, the first and the second signals being generated in response to differing positions of the first guidewire in the lumen;

recording respective correspondences between the first and second signals at each of the differing positions;

withdrawing the first guidewire from the lumen;

after withdrawing the first guidewire, advancing through the lumen a second guidewire, having a second diameter smaller than the first diameter, and being configured to be tracked by the impedance tracking system;

while advancing the second guidewire, receiving a third signal of the impedance tracking system generated in response to advancement of the second guidewire in the lumen; and applying the respective correspondences to the third signal in order to determine a position of the second guidewire in the lumen.

In an embodiment the first guidewire includes a coil configured generate the first signals in response to a magnetic field generated by the electromagnetic tracking system, and an electrode configured to inject a current into the patient so as to generate the second signals as a set of currents received by respective electrodes on skin of the patient.

In a disclosed embodiment the second guidewire is not trackable by the electromagnetic tracking system.

In a further disclosed embodiment the method includes, while withdrawing the first guidewire from the lumen, recording further respective correspondences between the first and second signals at each of the differing positions of the first guidewire in the lumen, and applying the further respective correspondences to the third signal in order to determine the position of the second guidewire.

There is also provided, according to an embodiment of the present invention embodiment, apparatus, consisting of:

a first guidewire having a first diameter and configured to be tracked by an electromagnetic tracking system and an impedance tracking system;

a second guidewire, having a second diameter smaller than the first diameter, and configured to be tracked by the impedance tracking system; and a processor, configured:

while the first guidewire is advanced through a lumen in the body of a patient, to record first signals of the electromagnetic tracking system and second signals of the impedance tracking system, the first and the second signals being generated in response to differing positions of the first guidewire in the lumen;

to record respective correspondences between the first and second signals at each of the differing positions;

after withdrawal of the first guidewire from the lumen, to receive a third signal of the impedance tracking system generated in response to advancement of the second guidewire in the lumen; and to apply the respective correspondences to the third signal in order to determine a position of the second guidewire in the lumen.

The present disclosure will be more fully understood from the following detailed description of the embodiments thereof, taken together with the drawings, in which:

DETAILED DESCRIPTION OF EMBODIMENTS

Overview

In many medical procedures where a guidewire is required to be inserted into a patient, it is difficult to accurately track the guidewire as it is inserted. The guidewire is typically used to deliver an element, such as a balloon catheter, to a desired location. Larger guidewires may be more easily tracked, since they may incorporate elements such as sensors assisting in the tracking. However, larger guidewires, together with the elements they deliver, may be more likely to cause trauma in the patient.

Embodiments of the present invention address this problem by using two guidewires, a first, mapping guidewire, and a second delivery guidewire. The delivery guidewire has a smaller diameter than the mapping guidewire. The mapping guidewire is configured to be tracked by an electromagnetic tracking system and an impedance tracking system, and while it is advanced into a lumen of a patient signals for the two systems are recorded. Correspondences between the two signals are recorded for differing positions of the mapping guidewire as it advances.

The mapping guidewire is then withdrawn and the delivery guidewire is inserted into the lumen. The delivery guidewire is configured to be tracked only by the impedance tracking system, which enables the delivery guidewire to have a smaller diameter than the mapping guidewire. The impedance tracking system, used as a stand-alone system, is typically less accurate than the electromagnetic tracking system. However, embodiments of the present invention overcome this inaccuracy by applying the correspondences recorded for the mapping guidewire to the impedance tracking system signals of the delivery guidewire, enabling the position of the delivery guidewire to be accurately determined.

System Description

Figure 1:
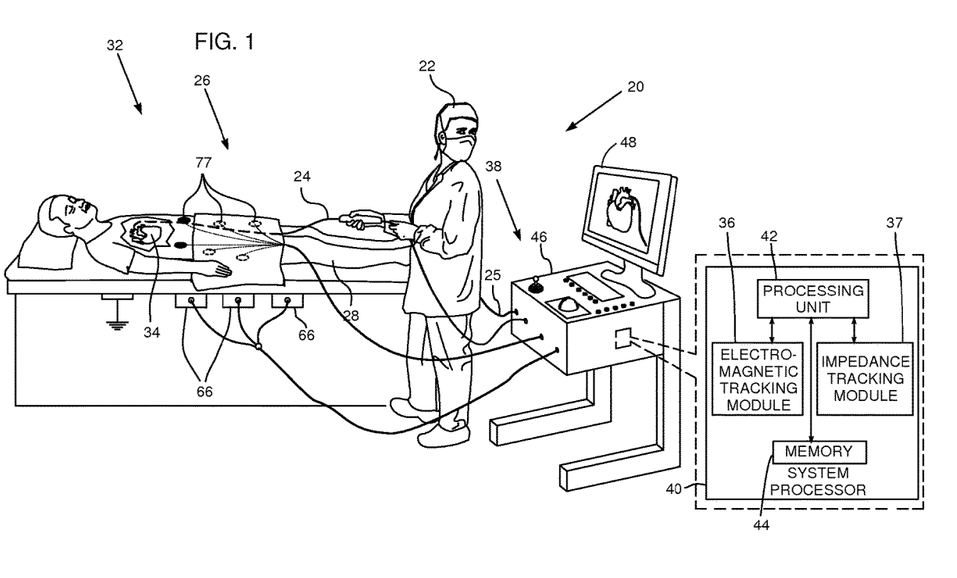
FIG. 1 is a schematic illustration of a guidewire tracking system, according to an embodiment of the present invention.

Reference is now made to FIG. 1, which is a schematic illustration of a guidewire navigation system 20, according to an embodiment of the present invention. For simplicity and clarity, the following description, except where otherwise stated, assumes an angioplasty procedure wherein an operator 22 of system 20, herein assumed to be a medical practitioner, inserts a guidewire into a lumen 26 of a patient 28. The angioplasty procedure may be indicated, for example, for a case of chronic total occlusion. Typically in the procedure, the guidewire is initially inserted into the patient until a distal portion 32 of the guidewire reaches a desired location in, or in proximity to a heart 34 of the patient.

Guidewire 24 is used to map the path followed by the guidewire to the desired location in the region of heart 34, so that during the guidewire insertion, the path followed by the distal portion is tracked. The guidewire is then withdrawn, and a second guidewire 25, smaller in diameter than guidewire 24, is inserted along the tracked path to the heart desired location. Second guidewire 25 is typically used to deliver a catheter, such as a balloon catheter, to the desired location at the heart. Guidewire 24 is also referred to herein as mapping guidewire 24, and guidewire 25 is also referred to herein as delivery guidewire 25. The mapping guidewire is described in more detail with reference to FIGS. 2, 3A, and 3B, and the delivery guidewire is described in more detail with reference to FIG. 4.

System 20 may be controlled by a system processor 40, comprising a processing unit (PU) 42 communicating with an electromagnetic tracking module 36 and an impedance tracking module 37. The functions of both modules are described in more detail below. PU 42 also communicates with a memory 44. Processor 40 is typically mounted in a console 46, which comprises operating controls 38, typically including a pointing device such as a mouse or trackball, that operator 22 uses to interact with the processor. The processor uses software stored in memory 44 to operate system 20. Results of the operations performed by processor 40 are presented to the operator on a display 48, which typically presents a visual representation of the paths taken by guidewire 24 and guidewire 25 in patient 28. The software may be downloaded to processor 40 in electronic form, over a network, for example, or it may, alternatively or additionally, be provided and/or stored on non-transitory tangible media, such as magnetic, optical, or electronic memory.

For tracking the path of guidewire 24, embodiments of the present invention use two tracking systems. A first tracking system comprises an electromagnetic tracking system, similar to that described in U.S. Pat. No. 6,690,963 to Ben-Haim et al., whose disclosure is incorporated herein by reference, and to that used in the Carto™ system produced by Biosense-Webster of Diamond Bar, Calif. The electromagnetic tracking system is under control of electromagnetic tracking module 36. The electromagnetic tracking system comprises a plurality of magnetic field generators, herein assumed to comprise three sets of generators 66, each set comprising three orthogonal coils, so that the plurality of generators comprises a total of nine coils. Generators 66 are placed in known locations beneath patient 28, the known locations defining a frame of reference of the generators. Module 36 controls, inter alia, the amplitude and frequency of the alternating magnetic fields produced by the generators.

The alternating magnetic fields interact with a coil, described in more detail below, located within guidewire 24 and at the distal portion of the guidewire, so as to generate alternating electropotentials in the coil, and the electropotentials are received as a signal by tracking module 36. The module, together with processing unit 42, analyzes the received signal, and from the analysis is able to determine a position, i.e., a location and an orientation, of the guidewire coil in the defined frame of reference.

In the electromagnetic tracking system processor 40 uses the location and orientation of the guidewire coil to track the distal portion of the guidewire.

A second tracking system comprises an impedance measuring tracking system, similar to that described in U.S. Pat. No. 8,456,182 to Bar-Tal et al., whose disclosure is incorporated herein by reference. The Carto™ system produced by Biosense-Webster of Diamond Bar, Calif. also uses an impedance measuring tracking system. The impedance measuring tracking system is under control of impedance tracking module 37.

The impedance measuring tracking system measures currents between an electrode, described in more detail below, located at the distal portion of guidewire 24, and a plurality of generally similar patch electrodes 77, also herein termed patches, which are positioned on the skin of patient 28 in the vicinity of the region in which the guidewire is operating. The currents between the guidewire electrode and the patches vary according to the location of the electrode, because of the different distances of the distal portion from the patches, which cause different impedances between the distal portion electrode and the different patches. Module 37 may be configured to generate an indication of the location from the different currents.

Typically the tracking by either or both of the systems may be presented visually on display 48, for example by incorporating an icon representing the guidewire distal portion into an image of patient 28, as well as a path taken by the icon.

Figure 2:
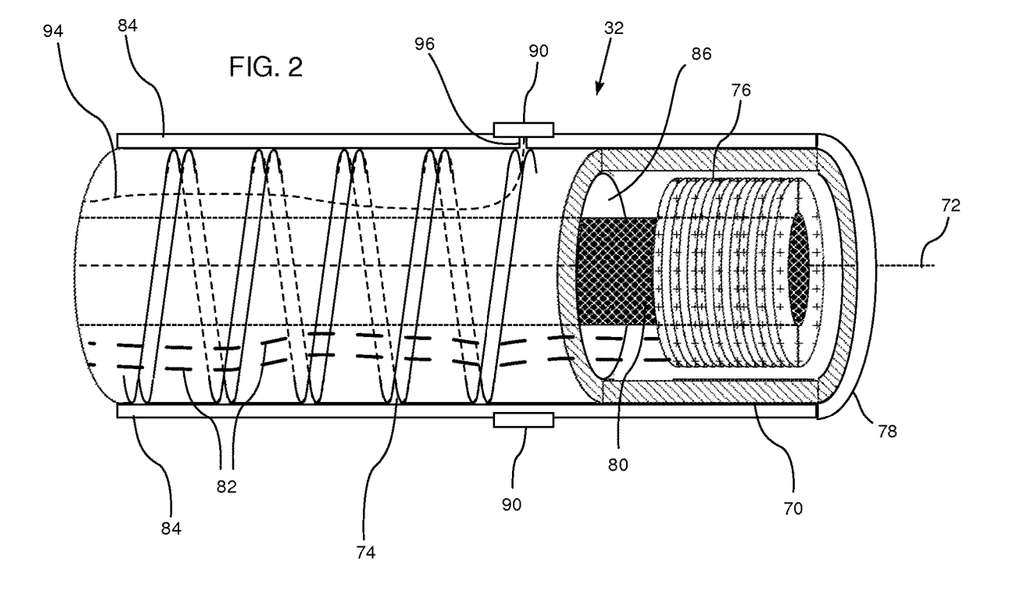
FIG. 2 is a schematic perspective diagram of a distal portion of a mapping guidewire, according to an embodiment of the present invention.
Figure 3A:
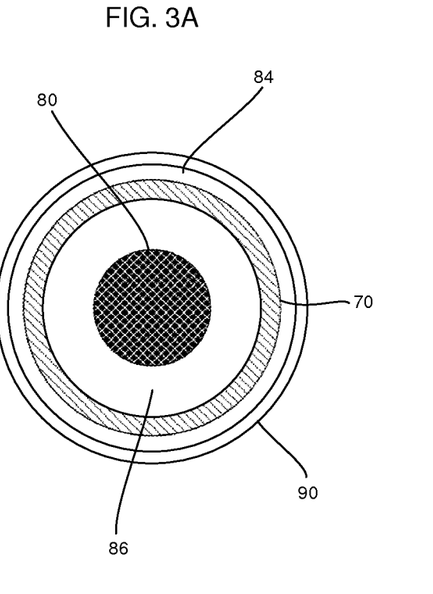
FIGS. 3A and 3B are schematic cross-sections of the mapping guidewire, according to an embodiment of the present invention.
Figure 3B:
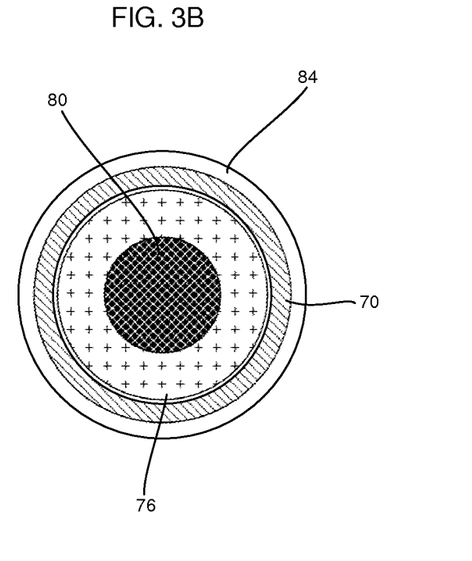

FIG. 2 is a schematic perspective diagram of distal portion 32 of mapping guidewire 24, and FIGS. 3A and 3B are schematic cross-sections of the guidewire, according to an embodiment of the present invention. In FIG. 2, a terminal portion of the distal portion has been cut-away to illustrate the internal structure of the guidewire. Guidewire 24 is formed from a hollow elastic metal tube 70, which has an internal longitudinal lumen 86 and an axis of symmetry 72. In a disclosed embodiment the material of the tube is a nitinol alloy, and the tube has an outer diameter of approximately 0.8 mm. and an inner diameter of approximately 0.5 mm. Tube 70 is formed into a helix, by having a laser cut a spiral channel 74 into the tube. Typically, when the tube is formed by laser cutting of the channel, the pitch of the channel is varied so that there are two or more different pitches. The different pitches give the guidewire the property that it has different flexibilities in different sections of the guidewire.

A small conductive coil 76, made of insulated wire, is inserted into lumen 86 so that it is located at a distal end 78 of the tube. FIG. 3B is a cross-section of guidewire 24 taken at the location of the coil. Prior to insertion the coil is wound on an elongate flexible core 80, herein assumed to comprise a wire, and also referred to herein as wire 80. After the coil has been formed the wire and coil are inserted into lumen 86, so that the wire lies approximately along axis 72, and so that the coil has a common axis of symmetry with axis 72. In the disclosed embodiment referred to above coil 76 has an external diameter of approximately 0.3 mm. Wires 82 connect the two ends of coil 76 to the proximal end of the guidewire, and proximal ends of the wires are connected to tracking module 36 so that the module receives an alternating electropotential signal generated in the coil. Module 36 is able to analyze the signal so as to determine the position of the coil, and thus the position of distal end 78.

The outer surface of tube 70 is covered by a thin layer 84 of biocompatible insulating polymer, the layer acting as a sleeve for the tube. Layer 84 prevents fluids from patient 28 contacting the outer surface of tube 70, and/or penetrating into lumen 86. The layer also acts to mechanically strengthen the guidewire. An electrode 90, typically in the form of a ring, is attached to and overlays layer 84. FIG. 3A is a cross-section of guidewire 24 taken at the location of the electrode. In some embodiments there may be more than one such electrode. An insulated wire 94 feeds from lumen 86, through spiral channel 74 and an aperture 96 formed in layer 84, and connects to the electrode. The wire conveys current between the electrode, via the proximal end of the guidewire, and module 37 and processing unit 42.

Figure 4:
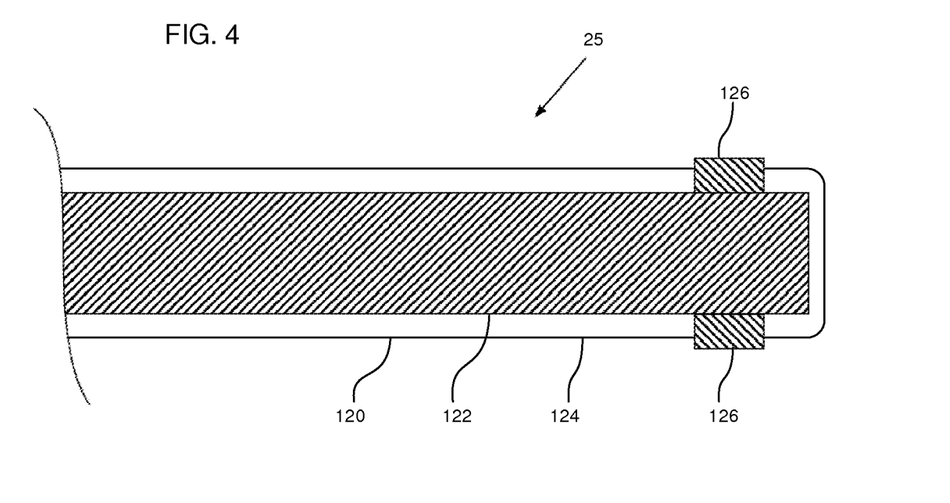
FIG. 4 is a schematic cross-section of a distal end of a delivery guidewire, according to an embodiment of the present invention.

FIG. 4 is a schematic cross-section of a distal end 120 of delivery guidewire 25, according to an embodiment of the present invention. Guidewire 25 has a circular cross-section. In contrast to mapping guidewire 24, delivery guidewire 25 does not have a conductive coil, and thus is not trackable by the electromagnetic tracking module. The absence of a conductive coil enables the diameter of the delivery guidewire to be significantly smaller than the diameter of the mapping guidewire. Delivery guidewire 25 is formed as a conductive elongate flexible core 122, typically a wire, and also referred to herein as wire 122. Wire 122 is covered by a thin layer 124 of biocompatible insulation polymer. A biocompatible conductive electrode 126 is formed at, or in close proximity to, the distal tip of the delivery guidewire, and is galvanically connected to wire 122. In some embodiments electrode 126 is in the form of a ring which is crimped onto wire 122.

As is described with reference to the flowchart of FIG. 5 below, current is injected from electrode 126 into patient 28, and currents received by patches 77 in response to the injected current are used to track the delivery guidewire.

Figure 5:
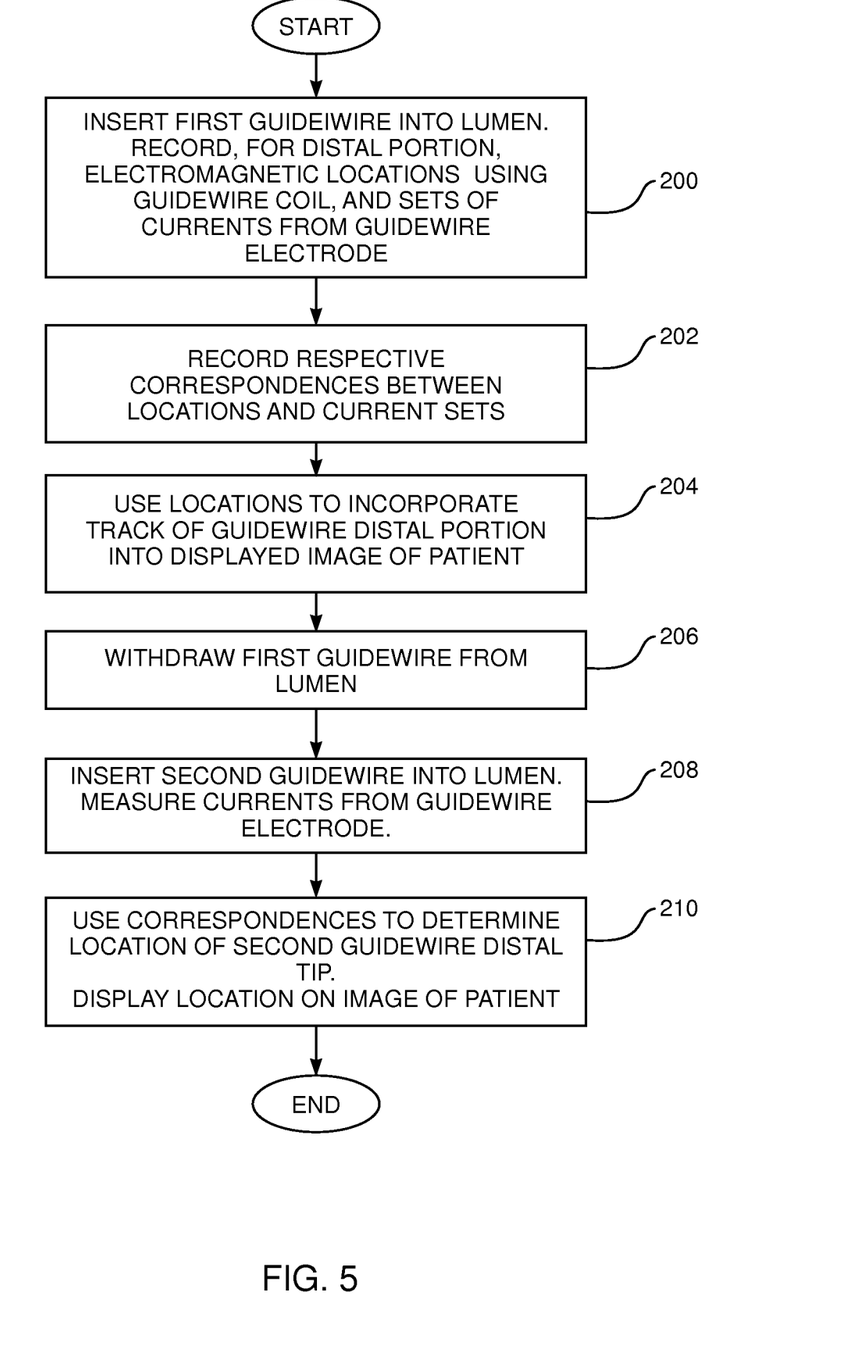
FIG. 5 is a flowchart of steps performed in implementing the system of FIG. 1, according to an embodiment of the present invention.

FIG. 5 is a flowchart of steps performed in implementing system 20, according to an embodiment of the present invention. In an initial step 200, mapping guidewire 24 is inserted into patient 28, and is advanced through a lumen of the patient, typically a vein, until distal portion 32 reaches a desired location, herein assumed to be in proximity to heart 34. While the guidewire is being advanced, its location within the patient is determined by electromagnetic tracking module from signals generated by coil 76. Also, while the guidewire is being advanced, impedance tracking module 37 injects an electric current from electrode 90 into patient 28, and records respective signals, in the form of sets of currents, received by patches 77 in response to the injected current.

In a relationship step 202, as the guidewire is being advanced, for each location determined by module 36 processor 40 registers the set of currents received by patches 77, and records a correspondence between the location and the set of currents. Thus, the processor records a multiplicity of correspondences between the locations of the guidewire and the registered current sets.

In a tracking step 204, also as the mapping guidewire is being advanced, processor 40 presents an image of the track of the distal portion of the guidewire on display 48. The track image is generated from the locations of the distal portion measured by the electromagnetic tracking system, i.e., by electromagnetic tracking module 36. The track image is typically superimposed on an image of the patient. The presentation enables operator 22 to follow the progress of the guidewire as it is inserted into the patient, and if necessary to correct the track followed by the guidewire.

Typically, the track image is maintained on display 48 for the remaining steps of the flowchart.

In a withdrawal step 206, once guidewire 24 has reached the desired location (in proximity to heart 34), the guidewire is withdrawn from the patient. Typically, during the withdrawal, both modules 36 and 37 operate, so that locations of the guidewire, and sets of currents received by patches 77, are again registered by processor 40. In this case, the processor may incorporate the locations and sets of currents acquired during the withdrawal into the multiplicity of correspondences recorded in step 202. Typically, such incorporation enhances the accuracy of the correspondences. The locations acquired during the withdrawal may also be used to enhance the accuracy of, and/or to correct, the track image on display 48.

In a second guidewire step 208, once mapping guidewire 24 has been withdrawn from the patient lumen, delivery guidewire 25 is inserted into, and advanced through, the lumen. While the delivery guidewire is being advanced impedance tracking module 37 injects a current from electrode 126 into patient 28, and the module records sets of currents received by patches 77 in response to the injected current.

In a final step 210, processor 40 treats each set of patch currents acquired in step 208 as a signal, and applies the correspondences recorded in the previous steps to determine a location of the delivery guidewire. The determined location may be imaged onto display 48, typically by overlaying the track of the delivery guidewire on the track of the mapping guidewire. The overlay enables operator 22 to see any deviation from the expected path, as well as to see the progress of the delivery guidewire.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

We claim:

1. A method, comprising:
advancing a first guidewire having a first diameter through a lumen in a body of a patient, the first guidewire being configured to be tracked by an electromagnetic tracking system comprising a conductive coil in said first guidewire and an impedance tracking system comprising an electrode on said first guidewire wherein said first guidewire is a mapping guidewire that does not include a catheter;
while advancing the first guidewire, recording first signals of the electromagnetic tracking system and second signals of the impedance tracking system, the first and the second signals being generated in response to differing positions of the first guidewire in the lumen;
recording respective correspondences between the first and second signals at each of the differing positions;
withdrawing the first guidewire from the lumen;
after withdrawing the first guidewire, advancing through the lumen a separate and unconnected second guidewire that is a delivery guidewire and includes a balloon catheter thereon, and having a second diameter smaller than the first diameter, and being configured to be tracked by the impedance tracking system;
while advancing the second guidewire, receiving a third signal of the impedance tracking system generated in response to advancement of the second guidewire in the lumen; and
applying the respective correspondences to the third signal in order to determine a position of the second guidewire in the lumen,
wherein the first guidewire is formed from a hollow elastic metal tube having an internal longitudinal lumen, wherein the material of the hollow elastic metal tube is a nitinol alloy, the hollow elastic metal tube being formed into a helix by cutting a spiral channel into the hollow elastic metal tube,
wherein a conductive coil made of insulated wire is provided in the internal longitudinal lumen, said conductive coil having a first end and a second end, said conductive coil being located at a distal end of the hollow elastic metal tube, the conductive coil being wound on an elongate flexible core wire, wherein the core lies along an axis of symmetry of the internal longitudinal lumen, wherein the conductive coil has a common axis of symmetry with the axis of symmetry of the internal longitudinal lumen, wherein two coil-connecting wires respectively connect the first end and the second end of the conductive coil to a proximal end of the first guidewire, wherein said two coil-connecting wires are connected to the electromagnetic tracking system.

2. The method according to claim 1, wherein the conductive coil is configured to generate the first signals in response to a magnetic field generated by the electromagnetic tracking system, and the electrode configured to inject a current into the patient so as to generate the second signals as a set of currents received by respective electrodes on skin of the patient.

3. The method according to claim 1, wherein the second guidewire does not comprise a coil.

4. The method according to claim 1, and comprising, while withdrawing the first guidewire from the lumen, recording further respective correspondences between the first and second signals at each of the differing positions of the first guidewire in the lumen, and applying the further respective correspondences to the third signal in order to determine the position of the second guidewire.

5. Apparatus, comprising:
a first guidewire having a first diameter and configured to be tracked by an electromagnetic tracking system comprising a conductive coil in said first guidewire and an impedance tracking system comprising an electrode on said first guidewire;
a separate and unconnected second guidewire that is a delivery guidewire and includes a balloon catheter thereon, and having a second diameter smaller than the first diameter, and configured to be tracked by the impedance tracking system; and
a processor, configured:
while the first guidewire is advanced through a lumen in a body of a patient, to record first signals of the electromagnetic tracking system and second signals of the impedance tracking system, the first and the second signals being generated in response to differing positions of the first guidewire in the lumen;
to record respective correspondences between the first and second signals at each of the differing positions;
after withdrawal of the first guidewire from the lumen, to receive a third signal of the impedance tracking system generated in response to advancement of the second guidewire in the lumen; and to apply the respective correspondences to the third signal in order to determine a position of the second guidewire in the lumen, wherein the first guidewire is formed from a hollow elastic metal tube having an internal longitudinal lumen, wherein the material of the hollow elastic metal tube is a nitinol alloy, the hollow elastic metal tube being formed into a helix by cutting a spiral channel into the hollow elastic metal tube, wherein a conductive coil made of insulated wire is provided in the internal longitudinal lumen, said conductive coil having a first end and a second end, said conductive coil being located at a distal end of the hollow elastic metal tube, the conductive coil being wound on an elongate flexible core wire, wherein the core lies along an axis of symmetry of the internal longitudinal lumen, wherein the conductive coil has a common axis of symmetry with the axis of symmetry of the internal longitudinal lumen, wherein two coil-connecting wires respectively connect the first end and the second end of the conductive coil to a proximal end of the first guidewire, wherein said two coil-connecting wires are connected to the electromagnetic tracking system.

6. The apparatus according to claim 5, wherein the the coil is configured to generate the first signals in response to a magnetic field generated by the electromagnetic tracking system, and the electrode is configured to inject a current into the patient so as to generate the second signals as a set of currents received by respective electrodes on skin of the patient.

7. The apparatus according to claim 5, wherein the second guidewire does not comprise a coil.

8. The apparatus according to claim 5, wherein the processor is configured, during withdrawal of the first guidewire from the lumen, to record further respective correspondences between the first and second signals at each of the differing positions of the first guidewire in the lumen, and to apply the further respective correspondences to the third signal in order to determine the position of the second guidewire.

* * * * *